United States Patent [19]

Okazaki

[11] Patent Number: 4,700,571
[45] Date of Patent: Oct. 20, 1987

[54] ULTRASONIC IMAGING APPARATUS

[75] Inventor: Kiyoshi Okazaki, Tochigi, Japan

[73] Assignee: Kabushiki Kaisha Toshiba, Kawasaki, Japan

[21] Appl. No.: 875,687

[22] Filed: Jun. 18, 1986

[30] Foreign Application Priority Data

Jun. 19, 1985 [JP] Japan .................................. 60-133421

[51] Int. Cl.⁴ .......................................... G01N 29/04
[52] U.S. Cl. ...................................... 73/597; 73/626; 128/660
[58] Field of Search ......................... 73/626, 628, 597; 128/660

[56] References Cited

U.S. PATENT DOCUMENTS

| 4,234,940 | 11/1980 | Iinuma | 73/626 |
| 4,528,854 | 9/1985 | Shimazaki | 73/626 |
| 4,542,653 | 9/1985 | Liu | 73/626 |
| 4,542,746 | 9/1985 | Takamizawa | 73/626 |
| 4,550,606 | 11/1985 | Drost | 128/660 |

*Primary Examiner*—Anthony V. Ciarlante
*Attorney, Agent, or Firm*—Finnegan, Henderson, Farabow, Garrett & Dunner

[57] ABSTRACT

An ultrasonic imaging apparatus has an ultrasonic transducer comprising an array of ultrasonic transducer elements which are divided into a transmission group and a reception group in an array direction. The transmission group transmits ultrasonic beams. The reception group receives ultrasonic beams crossing those transmitted by transmission group. When beams are transmitted to an object and reflected from the object are received, the velocity of the sound propagating through the object is measured. The voltage of drive pulses and that of echo pulses are detected, and the voltage dependency parameter of the drive pulses is calculated from the detected voltages. After each cycle of beam transmission/reception, the active positions of the transmission group and reception group are moved in the lengthwise direction of the array of transducer elements. Then, another cycle of beam transmission/reception is carried out, thereby detecting the voltage of drive pulses and that of echo pulses, and calculating the voltage dependency parameter of the drive pulses. Nonlinear parameters are calculated from the velocities of sound and voltage dependency parameters, which have been obtained by repeating the beam transmission/reception cycle. The nonlinear parameters and sound velocities are displayed.

9 Claims, 19 Drawing Figures

ULTRASONIC IMAGING APPARATUS

BACKGROUND OF THE INVENTION

The present invention relates to an ultrasonic imaging apparatus and, more particularly, to an ultrasonic imaging apparatus for performing diagnosis of living organism tissue by utilizing a nonlinear phenomenon and/or a sound velocity caused by an ultrasonic beam passing through a living organism tissue and/or the interaction between an ultrasonic wave and the living organism's tissue.

Various techniques using ultrasonic waves have been proposed for extracting information representing the state of living organism's tissue. A so-called cross-beam method has received a great deal of attention in recent years. This method can measure various acoustic and nonlinear parameters, sound velocity, etc. by crossing an ultrasonic transmission beam and an ultrasonic echo beam.

An ultrasonic diagnosis apparatus using the cross-beam method employs a conventional linear scanning type ultrasonic transducer. The ultrasonic transducer of this type has a transducer array including a large number of ultrasonic transducer elements. This transducer array is divided into first and second transducer groups spaced apart by a predetermined distance. The first and second transducer groups are switched to alternately perform transmission and reception. If the first transducer group serves as a transmission group, drive pulses are supplied to the transducer elements of this transducer group at such different timings as to cause it to emit ultrasonic beams into the living body at a predetermined angle. Waves reflected by the body (i.e., echo waves) are received by the second transducer group. During the transmission and reception operation, a propagation time of the ultrasonic wave from the transmission point to the reception point is measured, and at the same time, voltages of drive pulses are changed to measure a drive voltage dependency parameter of the echo wave received by the second transducer group. The drive voltage dependency parameter varies in accordance with the changes in drive pulse voltage. A nonlinear parameter is calculated from data of drive voltage dependency parameter. The calculated acoustic and nonlinear parameters are used to distinguish normal tissue from abnormal tissue.

In the conventional ultrasonic diagnosis apparatus described above, the data acquired by one cycle of transmission and reception is used as data concerning the state of the tissue in the ultrasonic wave propagation path. For this reason, the abnormal tissue cannot be easily discriminated from the normal tissue by the resultant parameter data.

In actual diagnosis, a wide range of tissue is of interest. In the above ultrasonic diagnosis apparatus, the ultrasonic wave propagation path must be mechanically changed, that is, the ultrasonic transducer must be moved along the body surface. This manipulation is very cumbersome, preventing improvement improvement of diagnostic efficiency.

SUMMARY OF THE INVENTION

It is an object of the present invention to provide an ultrasonic imaging apparatus wherein normal tissue can be easily distinguished from abnormal tissue, and effective diagnosis can be achieved.

According to the present invention, there is provided an ultrasonic imaging apparatus for measuring the sound velocity of an ultrasonic wave propogating through a tissue of an object to be investigated. The apparatus comprises an ultrasonic transducer means for transmitting ultrasonic waves to the object to be investigated, the transducer means including a plurality of ultrasonic elements arranged in a row, and means for driving the first transducer group of the ultrasonic transducer means to emit an ultrasonic transmission beam to a plurality of discrete areas of the object, the first transducer group including a predetermined number of transducer elements of the ultrasonic transducer means. There is further provided means, including a plurality of second transducer groups corresponding to the plurality of areas of the object which are spaced apart from the first transducer group, each of the second transducer groups having a predetermined number of transducer elements, for receiving a plurality of echo beams from the areas of the object impinged by each said transmission beam, the echo beams propagating in a direction crossing the direction of the transmission beams. The number of the second transducer groups is equal to the number of the areas of the object being investigated. There is further provided means for measuring the time from emission of the transmission beam from the first transducer group to reception of the corresponding echo beams at one of the second transducer groups for each of the received echo beams; and means for determining the sound velocity for each received echo beam propogating through the areas of the object to obtain a plurality of sound velocities, and means for displaying the sound velocities from the determining means.

DETAILED DESCRIPTION OF THE PREFERRED EMBODIMENTS

Figure 1:
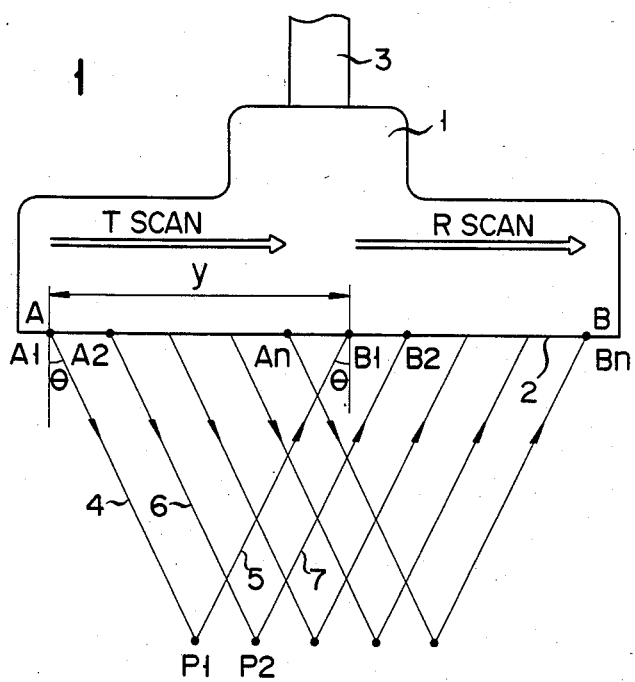
FIG. 1 is a schematic view showing cross-beam scanning by an ultrasonic transducer in an ultrasonic imaging apparatus according to an embodiment of the present invention.

FIG. 1 shows an example of object information extraction by a cross-beam. Referring to FIG. 1, ultrasonic transducer 1 comprises an array of a large number (e.g., 128) of ultrasonic transducer elements. The ultrasonic transducer array is divided into transmission section (Tscan) and reception section (Rscan). A predetermined number (e.g., 16) of transducer elements in transmission section (Tscan) is driven as a group having element A1 as the center. In this case, the transducer elements of the group are driven to emit ultrasonic beams along transmission path 4 inclined at angle $\theta$ with respect to the vertical axis of element A1. The ultrasonic wave reflected by object P1, i.e., the echo wave, is received by a transducer group having element B1 as center, along reception path 5.

Sound velocity $C_1 (=C)$ of the ultrasonic wave in the ultrasonic wave propagation path from A1 to B1 through P1 is calculated by equation (1) below:

$$C = y/(t \cdot \sin\theta) \quad (1)$$

where y is the distance between A1 and B1, and t is the propagation time of the ultrasonic wave propagating from A1 to B1.

In the above sound velocity calculation, since the sound velocity is unknown, angle $\theta$ is also unknown. In addition, since a reflector as object P does not exist in the organism, various processing procedures are required to calculate the sound velocity from equation (1).

Figure 2:
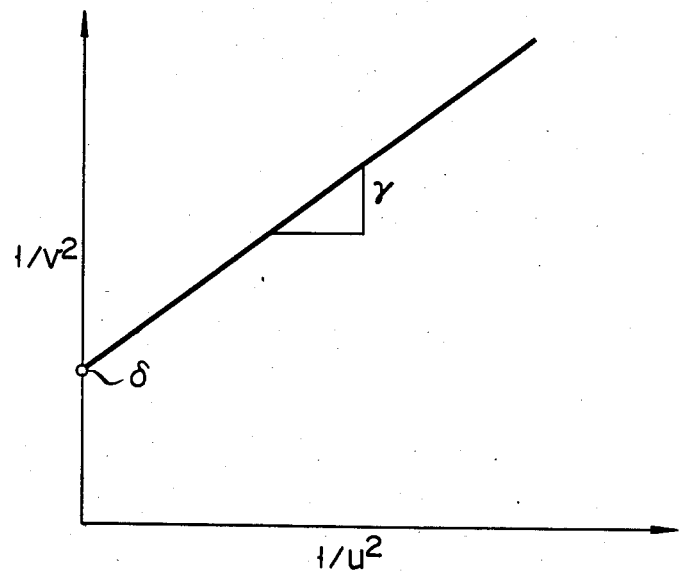
FIG. 2 is a graph showing the relationship between the drive voltage and the echo signal voltage.

In ultrasonic transmission and reception, when drive voltage is changed in level to drive the transducer elements in the transmission transducer group in an order of 10, 20, . . . 100 volts, amplitudes (volts) of the corresponding echo signals are measured and stored. Gradient $\gamma$ and value $\delta$ shown in FIG. 2 are calculated by equation (2) below:

$$1/v^2 = \gamma \times 1/u^2 + \delta \quad (2)$$

A drive voltage dependency parameter $(K = \delta/\gamma)$ is calculated from gradient $\gamma$ and value $\delta$. The following relation is established between K, a nonlinear parameter (B/A) and a sound velocity (C):

$$K = K_0(1 + B/2A)/C^2 \quad (3)$$

where $K_0$ is the frequency dependency constant.

Substitution of the sound velocity (C) and the drive voltage dependency parameter (K) from equation (2) into equation (4) yields the nonlinear parameter (B/A) below:

$$B/A = 2(K/K_0 \times C^2 - 1) \quad (4)$$

When the sound velocity $(C_1)$ and the drive voltage dependency parameter $(K_1)$ in the A1-P1-B1 path are calculated, a transducer group including 16 ultrasonic transducer elements having element A2 as the central element is driven. In this case, the corresponding ultrasonic beam is received by the transducer group having element B1 as its center through the A2-P2-B2 path, i.e., paths 6 and 7. By this transmission and reception cycle, the corresponding sound velocity $(C_2)$ and the corresponding drive voltage dependency parameter $(K_2)$ are calculated. Similarly, the active center of the transducer group is sequentially shifted to An, and thus n sound velocity signals and n drive voltage dependency parameters are calculated.

Figure 3:
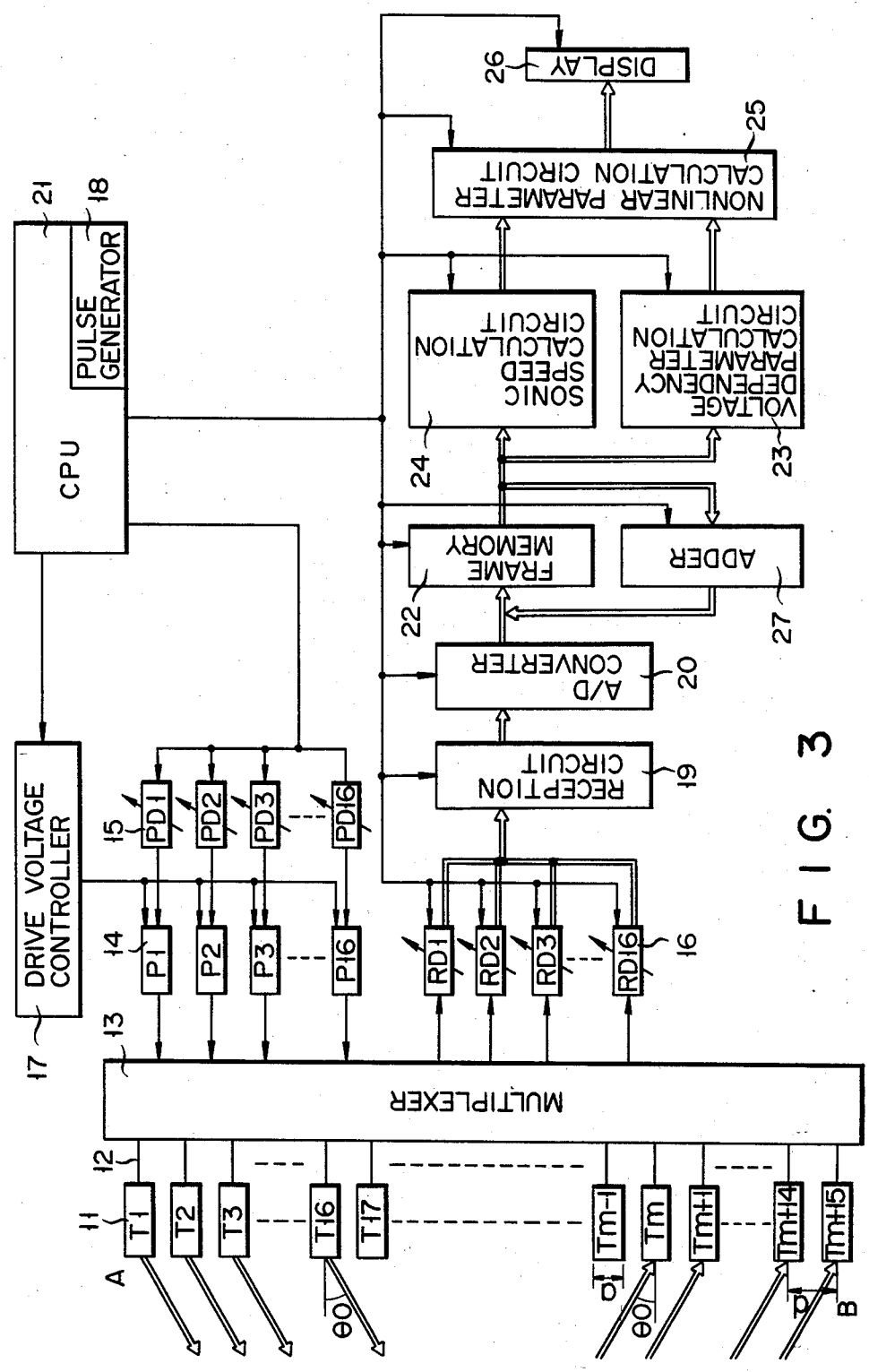
FIG. 3 is a block diagram of the ultrasonic imaging apparatus for performing cross-beam scanning in FIG. 1.
Figure 4:
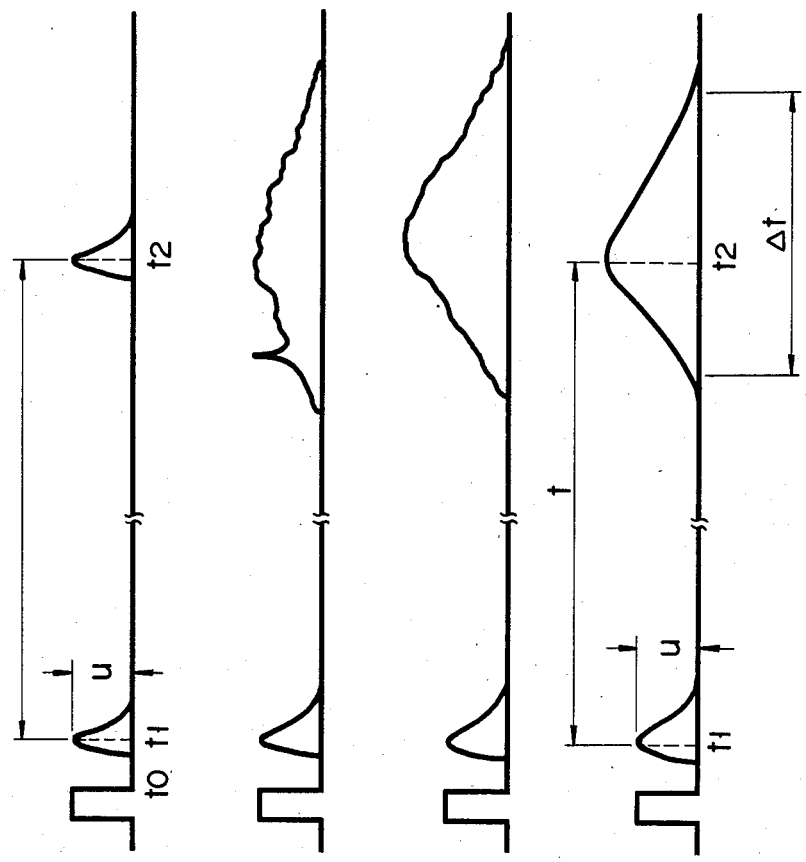
FIGS. 4a–d are timing charts of a transmission ultrasonic wave and the level of the echo wave.

The operation of the circuit in FIG. 3 will be described below. Transducer array 11 including 128 ultrasonic transducer elements (T1 to T128) is arranged on ultrasonic wave transmission/reception surface 2 of transducer 1. Transducer elements T1 to T128 have a width of 0.45 mm each. Distance d between the centers of each two adjacent ultrasonic transducer elements is 0.5 mm. Elements T1 to T128 are aligned and are connected to multiplexer 13 through lead wires 12 in cable 3.

CPU 21 includes pulse generator 18 for generating a 10-MHz reference clock and dividing the frequency of this reference clock to generate a 4-kHz pulse. The pulse output terminal of CPU 21 is connected to pulser circuit 14 having pulsers P1 to P16 through 16 transmission delay elements PD1 to PD16 of delay circuit 15. The output terminals of pulsers P1 to P16 are connected to multiplexer 13. Ultrasonic transducer 1 is brought into tight contact with, e.g., a patient's body surface through a coating material. If multiplexer 13 connects pulsers P1 to P16 to ultrasonic transducer elements T1 to T16 having element A1 as the center, ultrasonic waves generated from elements T1 to T16 are emitted onto the body. In this case, in order to emit the ultrasonic waves at angle $\theta$ with respect to the surface of the body, elements T1 to T16 can be driven by delay times $\tau_0$ calculated by equation (5), provided that sound velocity $C_0$ in the living organism is the same as that (1530 m/s) in water:

$$\tau_0 = (d/C_0) \cdot \sin\theta_0 \quad (5)$$

The delay times $\tau_0$ are respectively set in delay elements PD1 to PD16 of delay circuit 15. More specifically, delay elements PD1, PD2, PD3, ..., PD16 have delay times of $\tau_0, 2\tau_0, ..., 15\tau_0$, respectively.

If the sound velocity in the organism tissue is $C_0$ (i.e., the sound velocity in water), the ultrasonic beam propagates in the direction of $\theta_0$. However, in general, the sound velocity in the living organism is not limited to $C_0$ but may be C different from $C_0$. Therefore, the ultrasonic wave propagation direction is given by equation (6) according to Snell's law of refraction:

$$\sin\theta/C = \sin\theta_0/C_0 \quad (6)$$

After the ultrasonic pulses are emitted, multiplexer 13 connects 16 transducer elements Tm1 to Tm15 to reception delay circuit 16. Delay elements RD1 to RD16 in delay circuit 16 have the same delay times as delay elements T1 to T16 in transmission delay circuit 15. More specifically, delay times $15\tau_0, 14\tau_0, ..., \tau_0$, and 0 are respectively set in delay elements RD1, RD2, ..., RD15, and RD16.

The ultrasonic waves emitted from ultrasonic transducer elements T1 to T16 are reflected by object P1. The echo waves are incident on ultrasonic array 11. If the sound velocity in the organism tissue is $C_0$ (or C), the echo waves incident on transducer elements Tm1 to Tm15 at given angle $\theta_0$ are converted to echo signals. The echo signals are input to delay elements RD1 to RD16 through multiplexer 13. In this manner, when the sound velocity of the organism tissue is $C_0$ (or C), echo signals having directivity of $\theta_0$ or $\theta$ are supplied to reception circuit 19.

The echo signals are amplified and detected by reception circuit 19. The detected echo signals are then supplied to A/D converter 20. Digital echo signals from A/D converter 20 are stored in frame memory 22. Memory 22 is addressed in response to a 10-kHz pulse based on the rate pulse from CPU 21. Addresses corresponding to sampling components of the echo signals stored in memory 22 accurately match with sampling components extracted in units of 100 nanoseconds (ns) from the moment of emission of the ultrasonic pulses. The Peak value of the echo signals stored in memory 22 represent waves reflected by point P. Therefore, if memory address corresponding to the peak value is detected, the propagation time t from the peak value of the ultrasonic wave output pulse to the peak value of the echo wave can be determined.

Substitution of equation (6) in equation (1) yields equation (7) below.

$$C = \sqrt{yC_0/(t \cdot \sin\theta_0)} \quad (7)$$

Since y, $C_0$, and $\theta_0$ in equation (7) are known, sound velocity calculation circuit 24 can calculate sound velocity C using equation (7). Therefore, sound velocity C in the organism is calculated and displayed on display 26.

Figure 5:
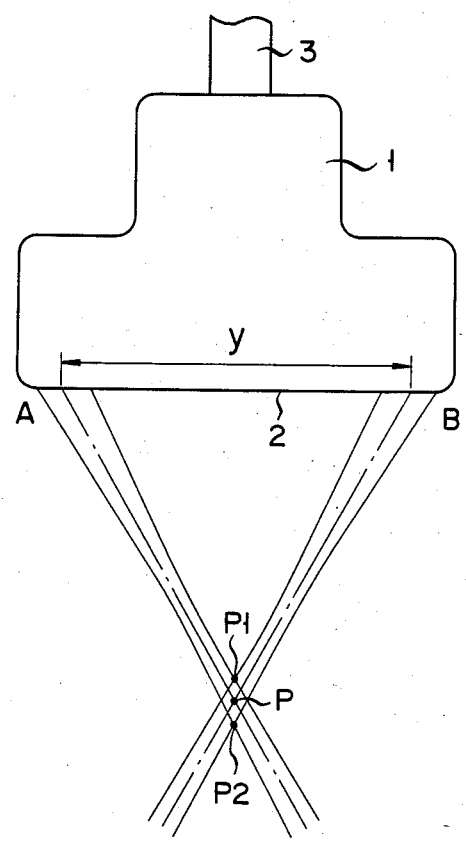
FIG. 5 is a schematic view showing a cross-beam.

As shown in the timing charts of FIGS. 4A to 4D, the ultrasonic pulse is output at a timing slightly delayed by time t0 representing the trailing edge of the drive pulse. The peak of the ultrasonic wave pulse is detected at time t1. As shown in FIG. 5, if point reflector P exists at an intersection between the center of the transmission ultrasonic beam and the center of the echo wave directed toward position B, a reflected wave having a peak at time t2, that is, an echo wave, can be obtained, as indicated by waveform in FIG. 4A. Ultrasonic wave propagation time t is calculated by time t1 at the peak of the transmission ultrasonic beam, and by time t2 at the peak of the echo wave.

Assume that relatively uniform liver tissue exists near target P. The resultant echo wave is a wave reflected by the liver tissue, located within the area defined by the intersection between the transmission ultrasonic beam and the echo beam directed toward position B. A reflected wave component of the reflected wave which reaches the ultrasonic transducer first corresponds to point P1 in FIG. 5. A reflecting wave component which reaches the ultrasonic transducer last is the one from point P2. In this case, the echo waves are spread, as indicated in FIG. 4B. Since the liver tissue is not completely uniform and has speckle components the echo waves have a random three-dimensional pattern. The peak value of such a waveform cannot be accurately detected, and transducer 1 must be slightly moved to shift the beam intersection in the liver by several hundreds of times. The resultant reflected wave data signals are sequentially added by adder 27. By this addition, the wave having the random three-dimensional pattern indicated in FIG. 4B can be smoothened to that indicated in FIG. 4C. If the peak value of the echo signal having waveform shown in FIG. 4C is detected, t2 can be determined. Therefore, the propagation time of the ultrasonic transducer can be calculated from $t = t2 - t1$.

If a 3.5-MHz ultrasonic wave is used and distance y is set to be 48 mm, the beam focused near intersection P has a width of 2 mm. This width corresponds to about 17% of the beam width at the wave transmission/reception section. Difference $\Delta t$ between the echo wave from P1 and that from P2 is about 4.5 $\mu$s. If $C = C_0$ and radiation angle $\theta 0$ is 30°, propagation time t is about 62.7 $\mu$s. A measurement error at time t2 for the peak value is assumed to be 1/10 or less. Therefore, a sound velocity measurement error is less than 10 m/s.

Drive Voltage Dependency Parameter (K) Measurement

The method of measuring this parameter (K) is basically the same as that for measuring the sound velocity, except for the following points. Drive voltage controller 17 for driving pulser circuit 14 changes drive voltage u under the control of CPU 21. Amplitudes v of echo signals from adder 27 are stored together with values of drive voltage u in frame memory 22. Data u and data v stored in frame memory 22 are read out and supplied to voltage dependency parameter calculation circuit 23 and are substituted into equation (2) to calculate values $\gamma$ and $\delta$. Finally, the voltage dependency parameter (K) is calculated.

Nonlinear Parameter (B/A) Measurement

As previously described, when the sound velocity (C) and the drive voltage parameter (K) are calculated, the calculated values are supplied to nonlinear parameter calculation circuit 25. Calculation circuit 25 calculates the nonlinear parameter (B/A) according to equation (4). In the same manner as described above, the sound velocity (C) and the nonlinear parameters (B/A) for all transmission/reception paths from the A1-P1-B1 path to the An-Pn-Bn path are obtained.

Figure 6:
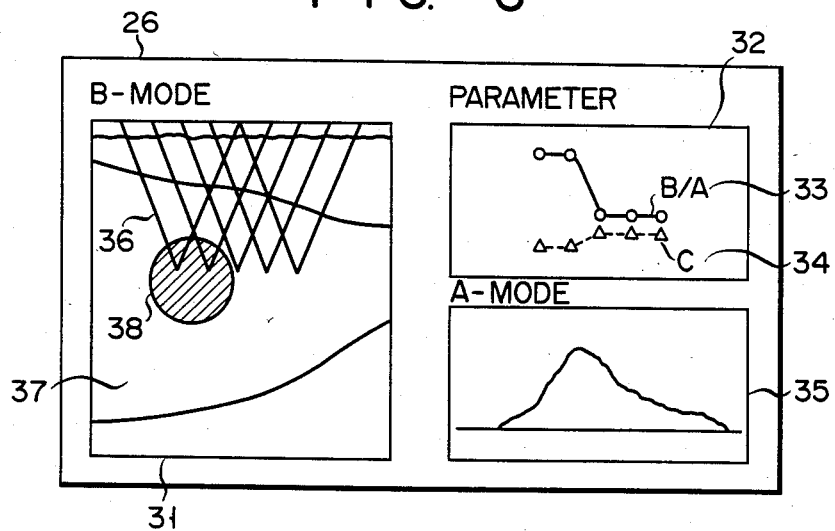
FIG. 6 is a plan view showing a monitor screen in the ultrasonic imaging apparatus of FIG. 3.

The sound velocity (C) and the nonlinear parameters (B/A) are supplied to and displayed on display 26. More specifically, sound velocity graph 34 and nonlinear parameter graph 33 are displayed on screen area 32, as shown in FIG. 6. The received wave signal pattern corresponding to waveform shown in FIG. 4D is also displayed on screen area 35. In addition, tomographic image (B-mode image) 31 is also displayed on the display screen by driving ultrasonic transducer 1 according to a conventional ultrasonic technique to obtain a tomographic image. Normal tissue image 37 and abnormal tissue image 38 are included in the image 31. Cross-beam path 36 is indicated at the top of image 31.

As is apparent from FIG. 6, by displaying the B-Mode image including information of the sound velocity (C), the nonlinear parameter (B/A), and the cross-beam path, the abnormal tissue can be easily distinguished from the normal tissue.

According to the above embodiment, the sound velocity (C) and the nonlinear parameter (B/A) of an internal organ of the living organism can be easily measured in a short period of time and in a noninvasive manner, without placing any load on a patient. The sound velocity (C) and the nonlinear parameters (B/A) obtained along different ultrasonic wave paths are calculated and displayed as one-dimensional graphs. Therefore, abnormal tissue can be easily distinguished from normal tissue.

In the above embodiment, CPU 21 controls transmission and reception delay circuits 15 and 16 and multiplexer 13 to perform known linear scanning in order to obtain a B-Mode image. In addition, it is possible to constitute an ultrasonic imaging apparatus that allows switching between the B-Mode image mode and the measuring mode by single operation.

Figure 7:
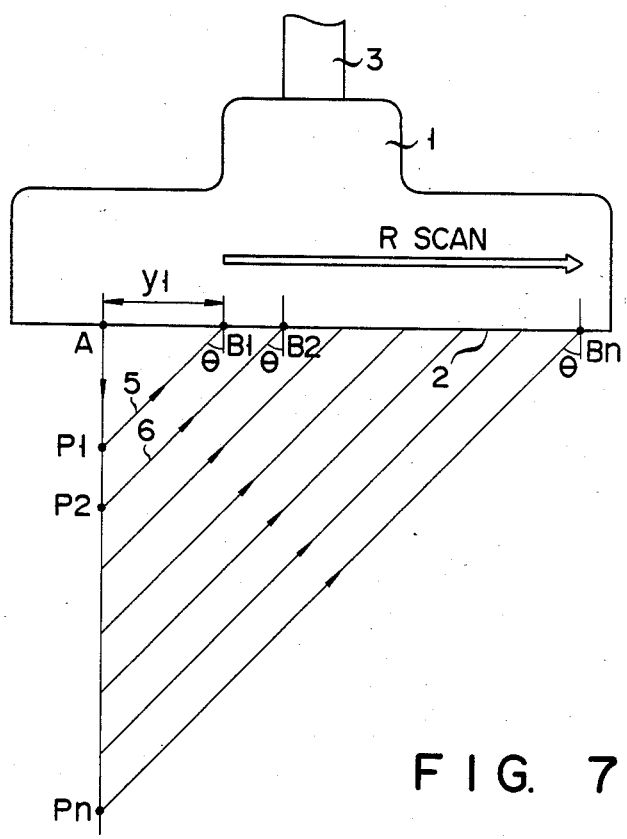
FIG. 7 is a schematic view showing cross-beam scanning in an ultrasonic transducer in an ultrasonic imaging apparatus according to another embodiment of the present invention.

In another embodiment of FIG. 7, a sound velocity and a nonlinear parameter along the direction of depth of the object are measured. In this case, a transducer group having position A as its center is driven and generates an ultrasonic beam propagating straight in the vertical direction ($\theta=0°$) from position A. An echo wave directed toward a transducer group having position B1 as its center, in the range of an echo wave of angle reflected by target P1, is received by this transducer group. During this transmission and reception cycle, a sound velocity ($C_1$) and a drive voltage dependency parameter ($K_1$) in an A-P1-B1 path are calculated. Distance y1 in the A-B1 path is known. If propagation time t of the ultrasonic wave through the A-P1-B1 path is calculated, sonic speed C in, e.g., liver tissue can be calculated by the following equation:

$$C = Y1/T \times (1/\sin\theta + 1/\tan\theta) \tag{1'}$$

Similarly, a sound velocity ($C_2$) and a drive voltage dependency parameter ($K_2$) in an A-P2-B2 path are calculated. By shifting the central position of the receiving transducer group slightly by a predetermined distance, n sound velocity values and n drive voltage dependency parameter values can be calculated.

In the same manner as in the above sound velocity measurement, an ultrasonic wave is vertically ($\theta=0°$) emitted from one end A of an ultrasonic wave reception surface onto the surface of, e.g., a patient's body, and propagates straight in the tissue along the A-P1 path. The ultrasonic wave is reflected by target P1. The reflected wave directed toward the transducer group having position B1 as its center is received by this group. In this case, amplitudes (volts) of the echo signals upon changing of pulse drive voltage in an order of, e.g., 10, 20, ..., 100 V are measured and stored. $\gamma$ and $\delta$ values are calculated by the following equation (2'):

$$1/v^2 = \gamma \times 1/u^2 + \delta \tag{2'}$$

Substitution of the $\gamma$ and $\delta$ values into $K=\delta/\gamma$ yields drive voltage parameter K. This parameter K has a relationship with the nonlinear parameter (B/A) and the sonic speed (C) as follows:

$$K = K_0(1 + B/2A)/C^2 \tag{3'}$$

where $K_0$ is a frequency dependency constant. The sound velocity (C) and the voltage dependency parameter (K) calculated by equations (1') and (2') are used to calculate a nonlinear parameter (B/A) according to equation (3'). In practice, the nonlinear parameter (B/A) is calculated by equation (4') below:

$$B/A = 2(K/K_0 \times C^2 - 1) \tag{4'}$$

Scanning for this embodiment, using the circuit of FIG. 8, will be described below. The transducer group having position A as its center, that is, transducer elements T1 to T16 are respectively connected by multiplexer 13 to pulsers P1 to P16. Pulsers P1 to P16 generate drive pulses in response to delay signals from delay elements PD1 to PD16. In this case, delay times $\tau_0$ between the delay elements are determined to emit the ultrasonic beam vertically ($\theta=0°$) onto the body surface according to equations (5) and (6) described herein.

When the ultrasonic waves are emitted from transducer elements T1 to T16, as shown in FIG. 7, the echo waves are incident on ultrasonic wave reception surface 2 of transducer 1. In this case, multiplexer 3 causes the transducer group having position B as its center, i.e., elements Tm1 to Tm16, to be connected to delay elements RD1 to RD16. Delay elements RD1 to RD16 have delay times for receiving the echo waves directed toward reception path 5 from position P1, that is, for receiving the echo waves incident at angle $\theta$. The delay times are calculated by equations (5) and (6).

The echo signals through delay elements RD1 to RD16 are received, amplified, and detected by reception circuit 19. The echo signals from reception circuit 19 are converted by A/D converter 20 to digital signals. The digital signals are then stored in frame memory 22.

In order to write echo data in memory 22, memory 22 is addressed in response to a 10-MHz clock with a precision of 100 ns.

The peak values of the echo data stored in memory 22 represent echo waves reflected by point P1. By detecting the memory addresses corresponding to the peak values, ultrasonic wave propagation time t1 from the ultrasonic wave transmission timing to the ultrasonic wave reception timing is determined. Time t1 is determined in consideration of the conditions described with reference to FIG. 4. When time t1 is determined, the sound velocity (C) of the ultrasonic wave propagating through the living organism can be calculated according to equation (7'), since y1, $C_0$, and $\theta_0$ are known:

$$C = \sqrt{-y1^2/t1^2 + 2y1/t1 \times C_0/\sin\theta_0} \quad (7')$$

sound velocities C respectively corresponding to positions B1 to Bn are thus calculated.

When sound velocities C are calculated, the drive voltage dependency parameters (K) are calculated in the same manner as for FIG. 1. More specifically, $\gamma$ and $\delta$ values are calculated according to equation (2'), and are then used to calculate drive voltage dependency parameter K. In this state, nonlinear parameter calculation circuit 25 performs equation (4') using the sound velocity ($C_0$) and the voltage dependency parameter (K) to calculate the nonlinear parameter (B/A).

Figure 8:
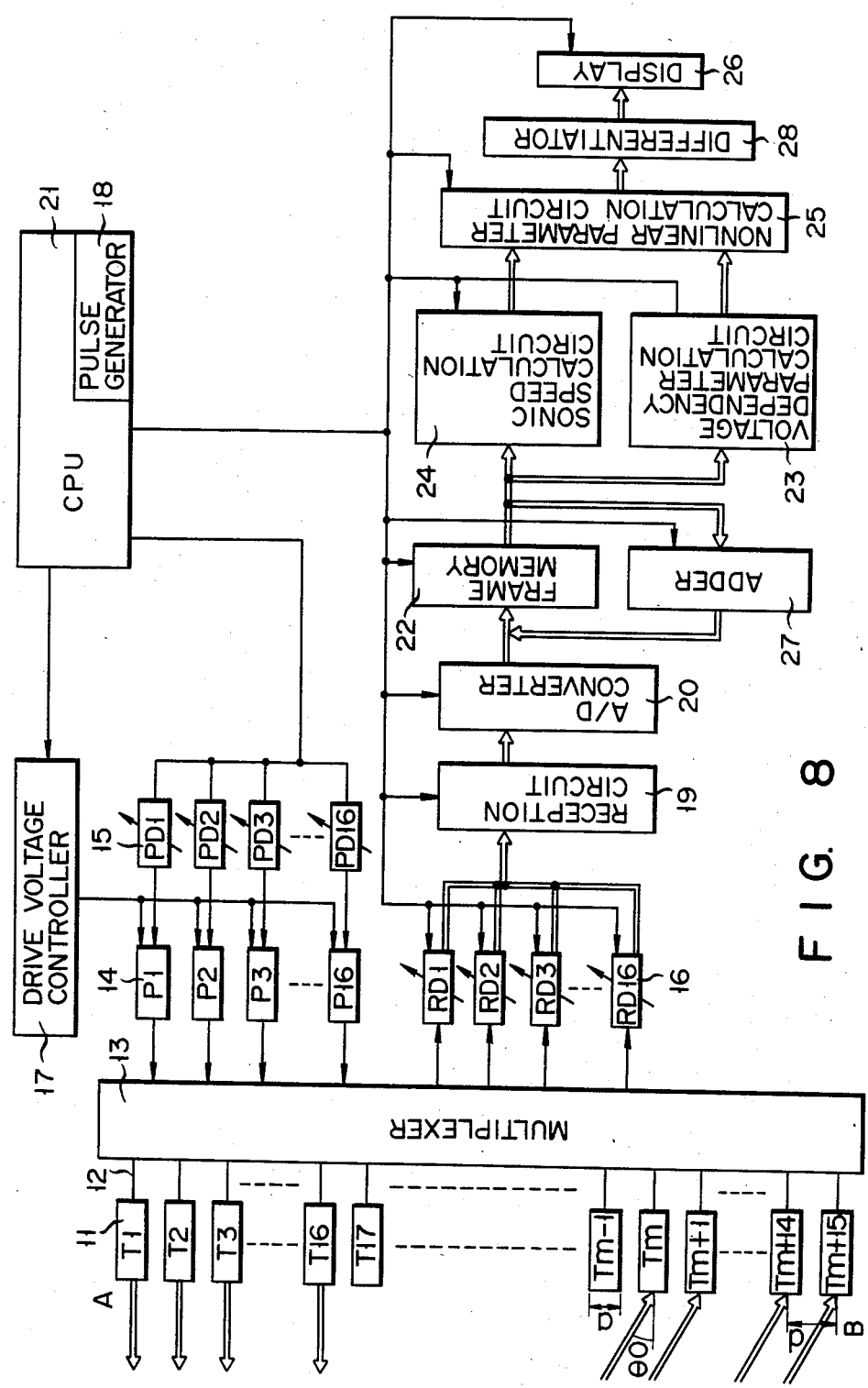
FIG. 8 is a block diagram of the ultrasonic imaging apparatus for performing cross-beam scanning in FIG. 7.

The nonlinear parameter (B/A) calculated by calculation circuit 25 and the sound velocity (C) are input to differentiator 28 in FIG. 8, and local sound velocity $C_{loc}$ and local nonlinear parameter $(B/A)_{loc}$ are calculated. Differences between sound velocity ($C_1$) in the 1-P1-B1 path and sound velocity $C_2$ in the A-P2-B2 path and between nonlinear parameter $(B/A)_1$ in the A-P1-B1 path and nonlinear parameter $(B/A)_2$ in the A-P2-B2 path are also calculated. Similarly, local sound velocities $C_{loc}$ and local nonlinear parameters $(B/A)_{loc}$ for point P2 and subsequent points are calculated.

Figure 9:
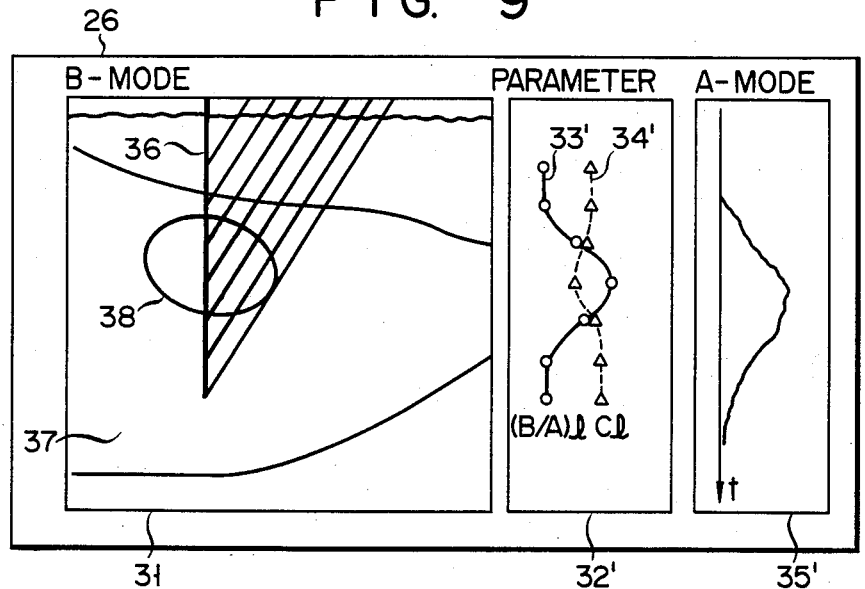
FIG. 9 is a plan view showing a monitor screen in the ultrasonic imaging apparatus of FIG. 8.

Local sound velocities $C_{loc}$ and local nonlinear parameters $(B/A)_{loc}$ are supplied to display 26. As shown in FIG. 9, patterns 34' and 33' of local sound velocities $C_{loc}$ and local nonlinear parameters $(B/A)_{loc}$ are displayed on screen area 32' of display 26. In this case, tomographic image (B-mode image) 31 and cross-beam path 36 are also displayed.

Figure 10:
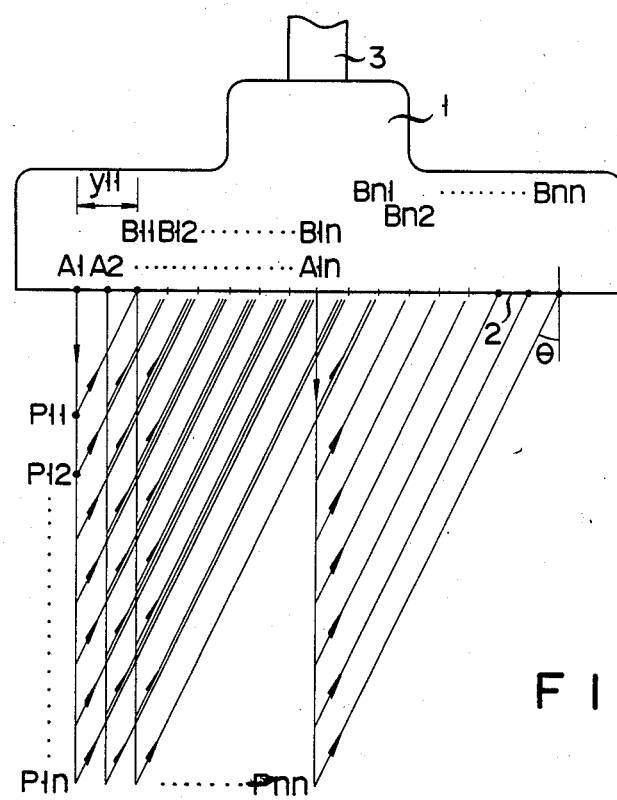
FIG. 10 is a schematic view showing cross-beam scanning in an ultrasonic transducer in an ultrasonic imaging apparatus according to still another embodiment of the present invention.

In still another embodiment of FIG. 10, vertical and horizontal sound velocities and nonlinear parameters are measured.

A transducer group having position A1 as its center on ultrasonic wave transmission surface 2 is driven to emit an ultrasonic pulse from position A1 to target P11. Echo waves from target P11 are received by a transducer group having position B11 as its center. In this case, a sound velocity ($C_{11}$) and a drive voltage dependency parameter ($K_{11}$) in an A1-P11-B11 path are calculated. Similarly, ultrasonic pulses sequentially emitted from position A1 are reflected by points P12 to P1n, and the echo waves are sequentially received by transducer groups having positions B12 to B1n as their centers. In these transmission and reception cycles, sound velocities and drive voltage dependency parameters are sequentially measured.

When the sound velocity and the drive voltage dependency parameter for the ultrasonic wave emitted from the transducer group having position A1 as its center are calculated, a sound velocity and a drive voltage dependency parameter for an ultrasonic wave emitted from a transducer group having position A2 as its center are then calculated. Similarly, sound velocities and drive voltage dependency parameters for ultrasonic waves from transducer groups up to the one having position A1n as its center are sequentially calculated.

In the embodiment of FIG. 10, the sound velocities and the drive voltage dependency parameters are calculated according to equations (1), (1'), (2), and (2'). Nonlinear parameters (B/A) are calculated according to equation (4).

Figure 11:
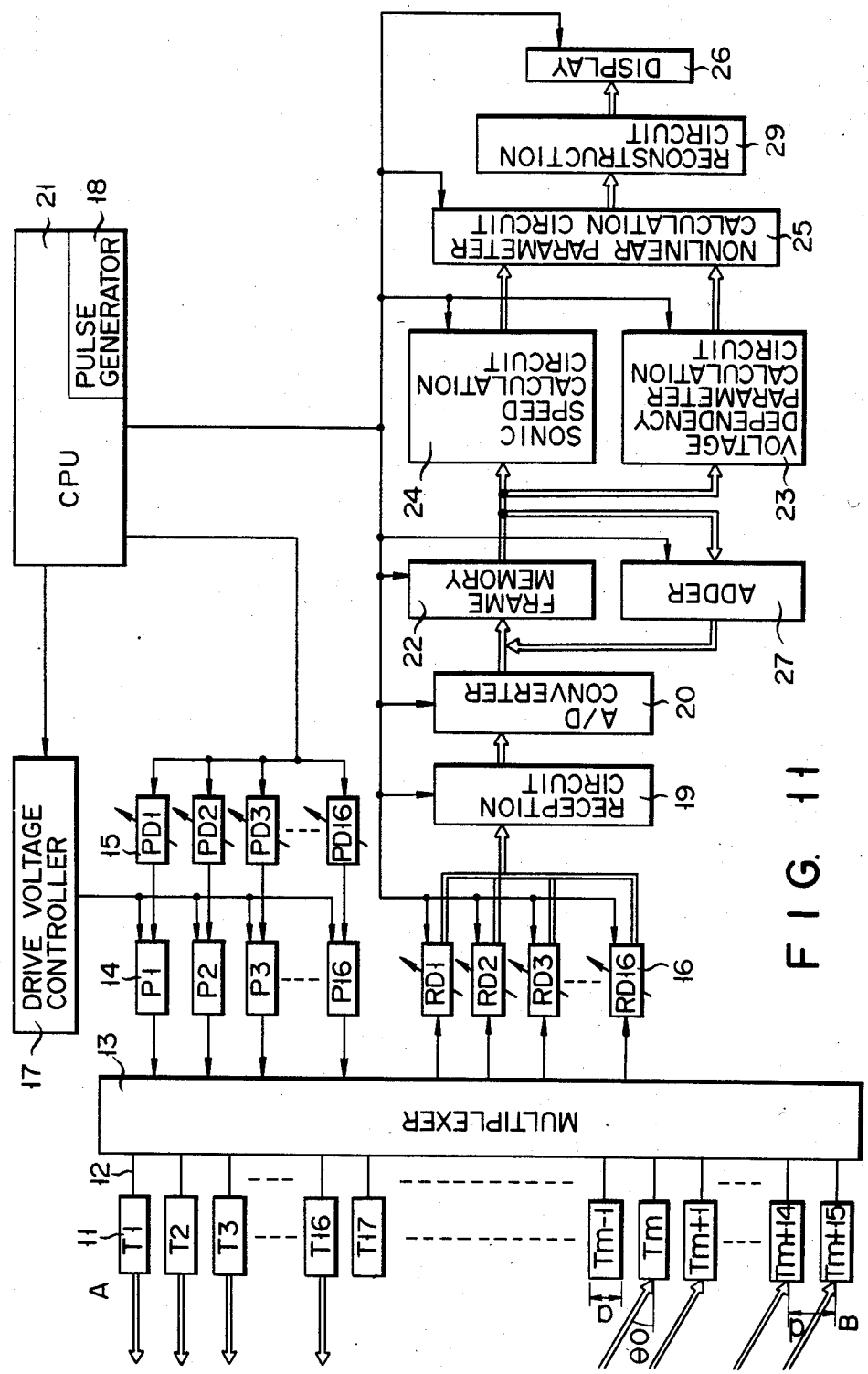
FIG. 11 is a block diagram of the ultrasonic imaging apparatus for performing cross-beam scanning in FIG. 10.

Scanning in the embodiment of FIG. 10 is performed by a circuit shown in FIG. 11. Ultrasonic pulses, the number of which corresponds to that of target points P11 to P1n, are generated from the transducer group having position A1 as its center. The reception transducer groups are switched in response to the corresponding ultrasonic pulses. For example, if transmission is switched from P11 to P12, reception is switched from B11 to B12. This switching operation is performed by multiplexer 13 controlled by CPU 21.

When measurement for the ultrasonic pulses from position A1 is completed, the transmission transducer group is switched from position A to position A2. This switching operation is also performed by multiplexer 13. When measurement for the ultrasonic pulses from the transducer group having position A2 as its center is completed, control is shifted to that having position A3 as its center. Finally, when control is shifted to the transducer group having position A1n as its center, the corresponding sound velocities and the corresponding voltage dependency parameters are measured. It should be noted that delay times in the transmission and reception cycles are determined as in the embodiment of FIG. 7.

The vertical and horizontal sound velocities and nonlinear parameters obtained above are supplied to reconstruction circuit (differentiator) 29 to sequentially calculate respective differences between the sound velocities and between the nonlinear parameters in each two adjacent ultrasonic paths. Local sound velocity $C_{loc}$ and local nonlinear parameters $(B/A)_{loc}$ are calculated as in the embodiment of FIG. 7.

Figure 12:
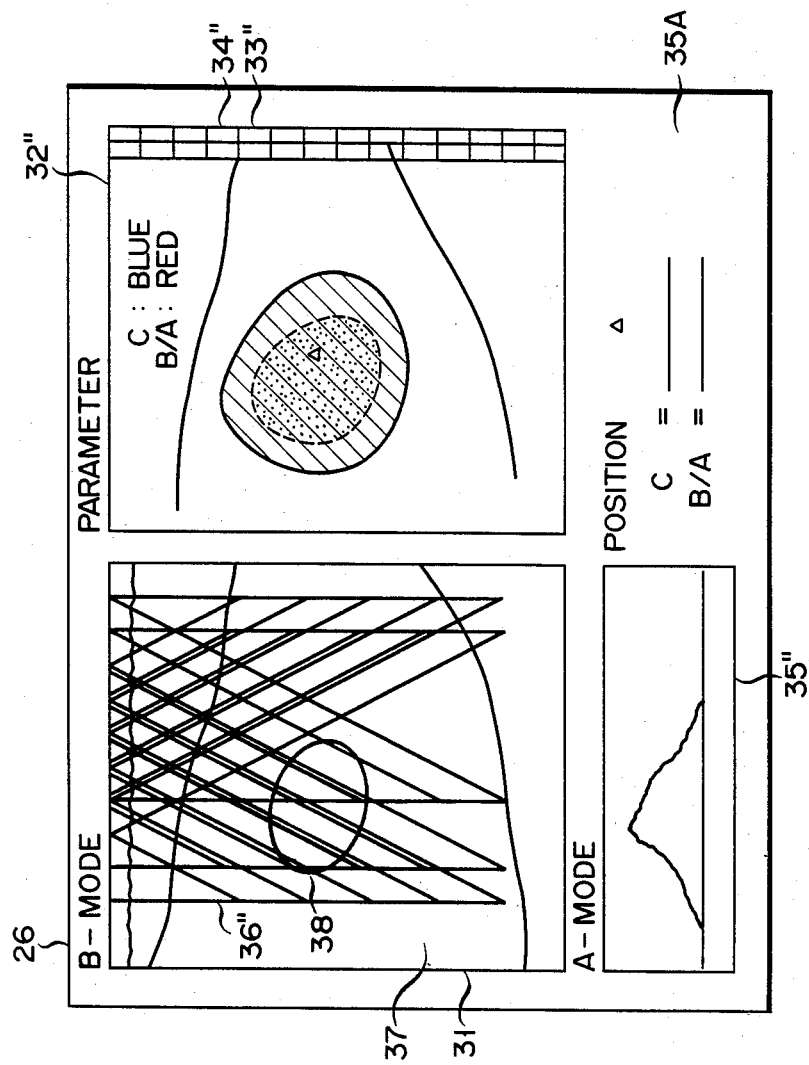
FIG. 12 is a plan view showing a monitor screen in the ultrasonic imaging apparatus of FIG. 11.

The vertical and horizontal sound velocities and nonlinear parameters are supplied to display 26 and the image shown in FIG. 12 is displayed thereon. More specifically, the sound velocity magnitudes are displayed as blue scale 34" with different brightness levels. Similarly, the nonlinear parameter magnitudes are displayed as red scale 33", also with different brightness levels.

Referring to FIG. 10, if an ultrasonic transducer group having position Bnn as its center is used for vertically emitting an ultrasonic wave and an ultrasonic transducer group having position Ain as its center is used for receiving an echo wave incident at angle $\theta$, scanning can be performed horizontally but in a direction opposite to that of FIG. 10. This switching operation can be performed by reversing the switching direction of multiplexer 13.

The echo wave pattern is displayed as image 35" and the sound velocity value and the nonlinear parameter value at the cursor point are displayed in display area 35A. Ultrasonic scan path 36", normal tissue 37 and abnormal tissue 38 are displayed in the area for displaying tomographic image 31.

Figure 13:
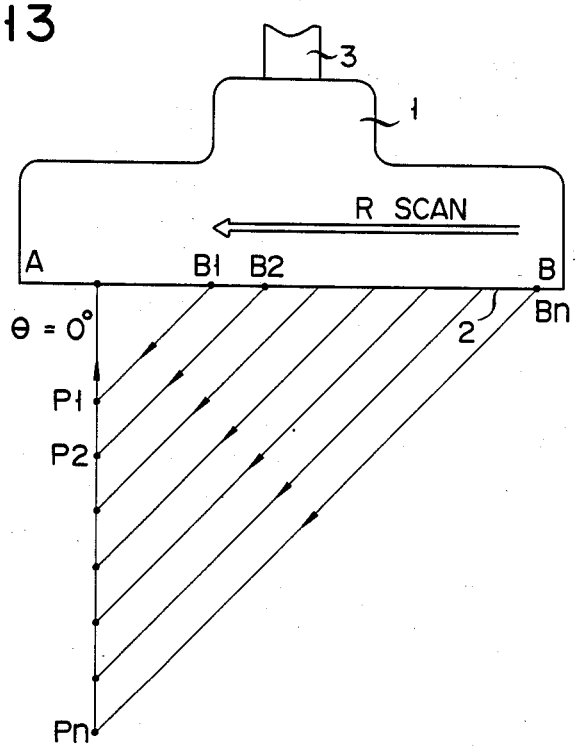
FIGS. 13 to 16 are schematic views showing cross-beam scannings in an ultrasonic transducer in an ultrasonic imaging apparatus according to still another embodiment of the present invention.

In still another embodiment shown in FIG. 13, the beam transmission/reception path is directed opposite to that in FIG. 7. More specifically, transducer groups having positions B1 to Bn as their respective centers are driven to transmit ultrasonic pulses at angle $\theta$ (e.g., 45°), and a transducer group having position A as its center receives echo signals which are incident at an angle of 0° thereon.

Figure 14:
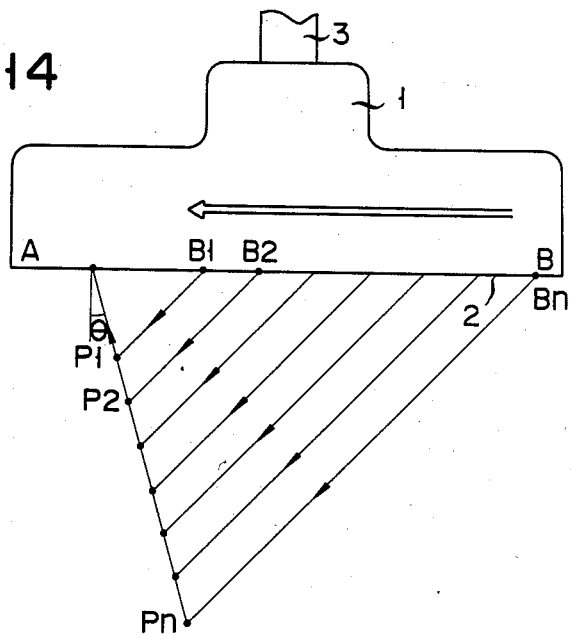
Figure 15:
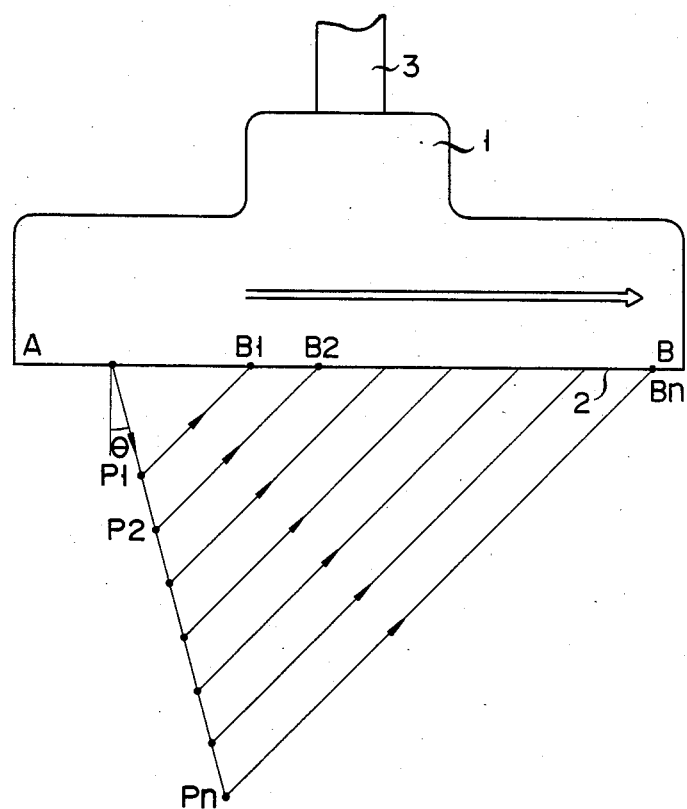

In the embodiment shown in FIG. 13, the wave reception angle is 0°. However, wave reception angle or wave transmission angle $\theta$ may vary within the range of $0° \leq \theta < 90°$ as shown in FIG. 14 or 15. If wave reception or transmission angle $\theta$ is 0°, an error accompanying ultrasonic wave incidence and reflection due to refraction or the like does not occur, and thus measurement data precision can be improved. In addition, under this condition, if the ultrasonic wave pattern is reversed about the center shown in FIG. 12 with angle $\theta$ being 0°, the scanning area can be the same as that in the B-Mode of linear scanning. Data for an identical field of view can thereby be acquired, improving diagnostic efficiency. In addition, at least one of the sound velocity and the nonlinear parameter is calculated and displayed.

Figure 16:
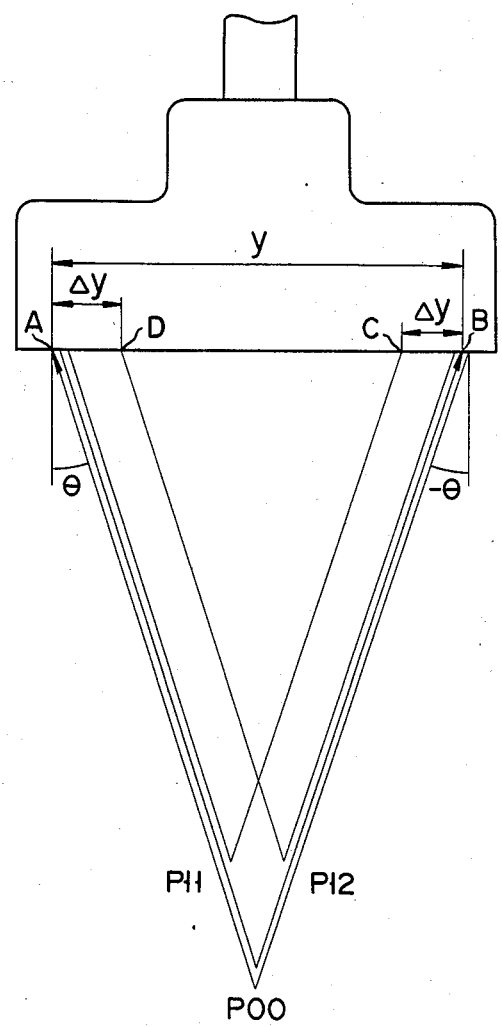

In the embodiment shown in FIG. 16, four beam transmission/reception paths, i.e., A - P00 - B, A - P11 - C, B - P00 - A, and B - P12 - D in order to measure the velocity of the sound propagating through abnormal tissue located within the triangle defined by points of reflection (measurement) P11, P12 and P00, points P11 and P12 being in an upper interface and point P00 being in a lower interface. Ultrasonic wave beams are transmitted and received by transducer 1 at both points A and B. An ultrasonic wave beam is transmitted from point A, reflected at point P00 and received at point B, and another beams is transmitted from point A, reflected at point P11 and received at point C. An ultrasonic wave beam is transmitted from point B, reflected at point P00 and received at point A, and another beam is transmitted from point B, reflected at point 12 and received at point D. The four transmission/reception paths are symmetrically located. The beams are transmitted from points A and B at angle $\theta$ and are received at points B and A at the same angle $\theta$. When ultrasonic beams are transmitted and received in this manner, the program and data required to form the image of the tissue can be simplified, facilitating the control of the ultrasonic imaging apparatus. Since the transmission/reception paths are symmetrically arranged, the data obtained from the received ultrasonic beams contain fewer errors. In this case, local sound velocities $C_{loc}$ of path P11-P00-P12 can be also measured from these four beams and scanning.

According to the present invention as described above, in ultrasonic wave transmission and reception by an ultrasonic transducer including an array of ultrasonic transducer elements, the array is divided into two transducer groups spaced apart by a predetermined distance and having the same number of transducer elements. The groups are selectively used as transmission and reception groups during cross-beam scanning. The cross-beam position is sequentially shifted. The propagation time of the ultrasonic beam from a transmission position to a reception position through a cross-beam position is then measured. A sound velocity of the ultrasonic wave through an object is calculated from the propagation time. In addition, a drive voltage dependency parameter is calculated from the transmission and reception voltages. A nonlinear parameter is calculated according to the sound velocity and the drive voltage dependency parameter. The sound velocity and the nonlinear parameter are then displayed on a display. With this display, normal tissue can be easily distinguished from abnormal tissue with reference to the displayed sound velocity and nonlinear parameter.

What is claimed is:

1. An ultrasonic imaging apparatus for measuring the sound velocity of an ultrasonic wave propogating through a tissue of an object to be investigated, said apparatus comprising:

an ultrasonic transducer means for transmitting ultransonic waves to the object to be investigated, said transducer means including a plurality of ultrasonic elements arranged in a row;

means for driving a first transducer group of said ultransonic transducer means to emit an ultrasonic transmission beam to a plurality of discrete areas of the object, said first transducer group including a predetermined number of transducer elements of said ultransonic transducer means;

means, including a plurality of second transducer groups corresponding to said plurality of areas of the object, said seoond transducer groups being spaced apart from said first transducer group and each of said second transducer groups having a predetermined number of transducer elements, for receiving a plurality of echo beams from said areas of the object, said echo beams propagating in a direction crossing the direction of said transmission beams, said second transducer groups being equal in number to the number of said plurality of areas of the object;

means for measuring the time from emission of said transmission beams from said transducer group to reception of the corresponding echo beams at one of said second transducer groups for each of said received echo beams;

means for determining the sound velocity for each received echo beam propogating through the areas of said object to obtain a plurality of sound velocities; and means for displaying the sound velocities from said determining means.

2. An apparatus according to claim 1, wherein said ultrasonic transducer means comprises transmission delay circuit means for outputting delay signals having transmission delay times determined in accordance with a predetermined emission angle of the ultransonic transmission beam, and driving means for supplying drive pulses to said transducer elements in response to the delay signals from said transmission delay circuit means in accordance with the transmission delay times, and said receiving means comprises reception delay circuit means for delaying echo signals to extract the echo signals corresponding to echo waves incident on said second transducer group from said areas of said object at said predetermined angle, and storage means for storing the echo signals through said reception delay circuit means.

3. An apparatus according to claim 2, wherein said transmission and reception delay circuit means comprises delay circuts for providing delay times for transmitting said transmission beam and receiving the echo wave at an identical angle.

4. An apparatus according to claim 2, wherein said transmission delay circuit means comprises a delay circuit for providing the delay times to cause said first transducer group to vertically emit said transmission from, and said reception delay circuit means comprises a delay circuit for providing the delay times to receive the echo wave reflected at a predetermined angle with respect to said transmission emission direction.

5. An apparatus according to claim 1, wherein said ultrasonic transducer means includes voltage control means for controlling a drive voltage for driving said first transducer group, said reception means includes means for measuring an echo signal voltage, said means for determining the sound velocity includes a first calculating means for calculating a drive voltage dependency parameter representing dependency of the echo signal voltage on the drive voltage and a second calculating means for calculating a nonlinear paramater in accordance with said drive voltage dependency parameter obtained by said first calculating means and said sound velocity, said nonlinear parameter being displayed on said display means.

6. An apparatus according to claim 1, wherein said means for driving said first transducer group includes means for horizontally shifting said transmission beam, and said receiving means comprises means for processing the echo signal to receive the echo wave corresponding to the transmission beam horizontally shifted.

7. An ultrasonic imaging apparatus for measuring the sound velocity of an ultrasonic wave propagating through a tissue of an object to be investigated, said apparatus comprising:
an ultrasonic transducer means for transmitting ultrasonic waves to the object to be investigated, said transducer means including a plurality of ultrasonic elements arranged in a row;
means for driving a first transducer group of said ultrasonic transducer means to emit an ultrasonic transmission beam to a plurality of discrete areas of the object, said first transducer group including a predetermined number of transducer elements of said ultrasonic transducer means;
means, including a plurality of second transducer groups corresponding to said plurality of areas of the object, said second transducer groups being spaced apart said first transducer group, each of said second transducer groups having a predetermined number of transducer elements, for receiving a plurality of echo beams from said areas of the object, said echo beams propagating in a direction crossing the direction of said transmission beams, said second transducer groups being equal in number to the number of said plurality of areas of the object;
means for measuring the time from emission of said transmission beams from said first transducer group to reception of the corresponding echo beams at one of said second transducer groups for each of said received echo beams;
means for determining the sound velocity for each received echo beam propagating through the areas of said object to obtain a plurality of sound velocities;
means for displaying the sound velocities from said determining means; and
switching means for switching at least one of said first and second transducer groups in an array direction to perform, respectively, ultrasonic transmission and reception from a shifted active position of respective first and second transducer groups.

8. An apparatus according to claim 7, wherein said switching means comprises means for connecting said transducer elements to said means for driving said first transducer group to generate said transmission beam at a sclected position from said first transducer group, and for sequentially switching said transducer elements corresponding to said second transducer group to sequentially receive the echo waves by sequentially shifting a receiving position for said echo waves, said time measuring means comprises means for sequentially measuring the ultrasonic wave propogation times of different transmission/reception paths according to the sequentially shifted receiving position, and said means for determining the sound velocity includes means for sequentially calculating the sound velocities from the ultrasonic wave propagation times and means for calculating a difference between the sound velocities of each two adjacent transmission/reception paths and for outputting said difference.

9. An apparatus according to claim 7, wherein said switching means comprises means for switching said transducer elements to horizontally shift said transmission beam from said first transducer group, and for sequentially switching said transducer elements corresponding to said second transducer group to sequentially receive the ebho waves from said areas of said object by sequentially shifting a receiving position of the echo wave, said time measuring means includes means for sequentially measuring the ultrasonic wave propagation times of different transmission/reception paths according to said sequentially shifted receiving position, and said means for determining the sound velocity includes means for sequentially calculating the sound velocities in accordance with said ultrasonic wave propagation times, and means for calculating a difference between the sound velocites of each two adjacent transmission/ reception paths and outputting said difference.

* * * * *